(12) United States Patent
Winneberger (10) Patent No.: US 11,540,884 B2
(45) Date of Patent: Jan. 3, 2023

(54) METHOD AND TRACKING SYSTEM FOR TRACKING A MEDICAL OBJECT (71) Applicant: Siemens Healthcare GmbH, Erlangen (DE)

(72) Inventor: David Winneberger, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 332 days.

(21) Appl. No.: 16/050,031

(22) Filed: Jul. 31, 2018

(65) Prior Publication Data

US 2019/0046275 A1 Feb. 14, 2019

(30) Foreign Application Priority Data

Aug. 8, 2017 (EP) .................................... 17185328

(51) Int. Cl.
*A61B 34/20* (2016.01)
*G06T 7/00* (2017.01)
(Continued)

(52) U.S. Cl.
CPC .......... *A61B 34/20* (2016.02); *A61B 5/02028* (2013.01); *A61B 5/349* (2021.01);
(Continued)

(58) Field of Classification Search
CPC ......... A61B 34/20; A61B 90/37; A61B 90/98; A61B 5/02028; A61B 5/0452;
(Continued)

(56) References Cited

U.S. PATENT DOCUMENTS 5,423,742 A * 6/1995 Theron ................ A61M 25/104
604/101.01
2004/0199151 A1* 10/2004 Neuberger ............. A61B 18/24
606/9

(Continued)

FOREIGN PATENT DOCUMENTS

CN 101297756 A 11/2008
CN 101453946 A 6/2009
(Continued)

OTHER PUBLICATIONS

European Search Report for corresponding Application No. 17185328. 6-1122, dated Jan. 26, 2018.
(Continued)

*Primary Examiner* — Joseph M Santos Rodriguez
*Assistant Examiner* — Kaitlyn E Sebastian
(74) *Attorney, Agent, or Firm* — Lempia Summerfield Katz LLC (57) ABSTRACT

The disclosure relates to a method and a tracking system for tracking a medical object. Herein, image data obtained by an imaging method and a predetermined target position is acquired for the medical object. The image data is used to detect the medical object automatically by an image processing algorithm and track the position thereof in a time-resolved manner. Furthermore, it is furthermore indicated when, or that, the detected medical object has reached the target position. A plurality of the detected positions of the medical object and associated detection times are stored in a database.

12 Claims, 2 Drawing Sheets

(51) Int. Cl.
*G06T 1/00* (2006.01)
*A61B 5/02* (2006.01)
*A61B 5/0452* (2006.01)
*A61B 90/00* (2016.01)
*A61B 90/98* (2016.01)
*A61B 5/349* (2021.01)
*A61B 17/00* (2006.01)
*A61B 34/00* (2016.01)
*A61B 34/30* (2016.01)

(52) U.S. Cl.
CPC .............. *A61B 90/37* (2016.02); *A61B 90/98* (2016.02); *G06T 1/0014* (2013.01); *G06T 7/0016* (2013.01); *A61B 2017/00703* (2013.01); *A61B 2034/2065* (2016.02); *A61B 2034/252* (2016.02); *A61B 2034/303* (2016.02); *A61B 2090/376* (2016.02); *G06T 2207/30048* (2013.01)

(58) Field of Classification Search
CPC .. A61B 2017/00703; A61B 2034/2065; A61B 2034/252; A61B 2034/303; A61B 2090/376; G06T 1/0014; G06T 7/0016; G06T 2207/30048; G06T 7/246; G06T 7/73; G06T 19/003; G06T 2207/30101; G06T 2210/41; G06T 2207/10081
See application file for complete search history.

(56) References Cited

U.S. PATENT DOCUMENTS

| | | | | |
|---|---|---|---|---|
| 2005/0228273 A1* | 10/2005 | Tamakoshi | ............ | A61B 6/548 600/425 |
| 2007/0248262 A1* | 10/2007 | Boese | .................... | A61B 90/36 382/154 |
| 2008/0300478 A1 | 12/2008 | Zuhars et al. | | |
| 2009/0306497 A1 | 12/2009 | Manzke et al. | | |
| 2010/0030061 A1 | 2/2010 | Canfield et al. | | |
| 2010/0121190 A1* | 5/2010 | Pagoulatos | ............ | A61B 5/061 600/437 |
| 2010/0179418 A1 | 7/2010 | Mueller et al. | | |
| 2012/0083652 A1* | 4/2012 | Langlois | ................ | A61B 5/064 600/103 |
| 2013/0226277 A1* | 8/2013 | Sun | ........................... | A61F 2/92 623/1.11 |
| 2014/0135744 A1 | 5/2014 | Stein et al. | | |
| 2014/0228678 A1 | 8/2014 | Meyer et al. | | |
| 2014/0369465 A1* | 12/2014 | Meyer | .................... | A61B 6/488 378/42 |
| 2015/0098550 A1* | 4/2015 | Yi | ........................ | A61B 6/4233 378/62 |
| 2016/0148372 A1* | 5/2016 | Itu | .......................... | A61B 5/026 382/128 |
| 2016/0302747 A1* | 10/2016 | Averbuch | ............. | A61B 6/5205 |
| 2017/0367776 A1* | 12/2017 | Kwok | ................ | A61B 18/1492 |
| 2018/0098820 A1* | 4/2018 | Park | ..................... | A61B 5/1079 |
| 2019/0021693 A1* | 1/2019 | Bharat | ................. | A61B 8/4411 |

FOREIGN PATENT DOCUMENTS

| | | |
|---|---|---|
| CN | 101879346 A | 11/2010 |
| CN | 103189013 A | 7/2013 |
| WO | WO2006051523 A2 | 5/2006 |
| WO | WO2012057871 A1 | 5/2012 |

OTHER PUBLICATIONS

Chinese Office Action for Chinese Application No. 201810883762.9 dated Jul. 8, 2021.

* cited by examiner

METHOD AND TRACKING SYSTEM FOR TRACKING A MEDICAL OBJECT

The application claims the benefit of European Patent Application No. EP 17185328.6, filed Aug. 8, 2017, which is hereby incorporated by reference in its entirety.

TECHNICAL FIELD

The disclosure relates to a method and a tracking system for automatic tracking of a medical object.

BACKGROUND

Nowadays, medical methods may be very complex and may include the use of numerous different medical objects, such as instruments, tools, and implants. At the same time, the need or the desire for data-driven analysis is constantly increasing in numerous areas of industry, technology and application—including the field of medical applications. To date, the methods available to date in the field may have been very intensive in terms of time and effort and, if used at all, may result in incomplete and error-prone data acquisition.

SUMMARY AND DESCRIPTION

The scope of the present disclosure is defined solely by the appended claims and is not affected to any degree by the statements within this description. The present embodiments may obviate one or more of the drawbacks or limitations in the related art.

It is the object of the present disclosure to facilitate improved and more effectively analyzed workflows in medical fields of application.

A method according to the disclosure is used to track a medical object. Herein, image data obtained by a medical imaging method is acquired continuously. This may refer to recording a series of X-ray, angiography, or tomography images, or the like and also reading corresponding image data from a data memory or receiving the image data by a data-processing device or the like. Furthermore, a predetermined target position for the medical object is acquired. This may refer to acquiring a user input or reading a data memory in which the target position is stored electronically. It may also be possible to determine the target position automatically, for example, by processing or evaluating the image data. It is also possible to use or take account of supporting data for this. Such supporting data may relate to or indicate a type of medical object and/or a respective type of procedure carried out while using the medical object. This data may also be obtained, for example, by acquiring corresponding user input or reading a corresponding data memory.

In a further method act, the medical object is automatically detected and time-resolved tracking of the respective position thereof is performed using the image data by an image processing algorithm. In other words, therefore, the image data is processed or evaluated in order to detect or recognize the medical object in the image data. For this, at a respective recording time of the image data, the medical object is obviously located in a recording region acquired or depicted thereby. Time-resolved tracking of the position of the medical object indicates that the respective position of the medical object at the respective time is acquired or determined together with the time over several times. Thus, it is possible to determine a spatially and temporally determined path or trajectory of the medical object. Herein, the respective position of the medical object may be determined relative to a basically arbitrary predetermined reference point in an arbitrary predetermined coordinate system. The position may be determined in a fixed coordinate system relative to a recording device used to record the image data or relative to an examination object, for example a patient, that is also at least partially acquired or depicted by the imaging method or by the image data.

Particularly, the position of the medical object may be determined relative to an anatomical feature of a patient depicted by the image data or a predetermined mark or reference position. This reference position may be the acquired target position. Thus, it is, for example, particularly simple to determine a distance of the medical object in its respective present position to the target position. The image processing algorithm may include an object-recognizing act. Thus, the image processing algorithm may enable the medical object to be recognized as well as the anatomical feature. It may be particularly advantageous to use as, or as part of, the image processing algorithm or for the execution thereof, a neural network, in particular a convolutional neural network because the use of a correspondingly trained neural network may facilitate particularly good adaptation to a respective application and hence particularly reliable object recognition.

In a further method act, it is indicated that, or when, the detected medical object has reached the target position. The fact that the medical object has reached the target position, may also be ascertained by the, or an, image processing algorithm. It is also, for example, possible for respective coordinates of the target position to be automatically compared with respective coordinates of the respective present position of the medical object. If this comparison produces a difference lying below a predetermined threshold value, this may be interpreted as reaching the target position.

In a further method act, some or all of the detected positions of the medical object and the associated detection times are stored in a database. In other words, therefore, the determined spatially and temporally defined path or trajectory of the medical object may be stored in the database. It is also possible for the respective target position to be stored in the database. In addition, it may be particularly advantageous to store predetermined and/or automatically recognized events with a respective entry time or recognition time in the database. Due to the larger database, this then advantageously facilitates a particularly exact and informative analysis of a respective process, for example a respective procedure performed using the medical object.

The medical object may be a catheter, a stent, a medical screw, or the like. In individual cases, the medical objects or types of medical objects that may be tracked may depend on the respective imaging method used. It may be particularly advantageous to detect and track a plurality of medical objects in the image data. For example, it is automatically possible for a catheter introduced into a patient or a subregion of the patient depicted by the imaging method to be automatically detected and tracked. The target position may be a midpoint of a stenosis that is marked, e.g., specified, or determined automatically using the image data. It is possible that a stent may already be arranged in the region of the stenosis, wherein the stent may also be automatically detected, recognized, and tracked as a further medical object.

It is then possible to track a route or journey, (e.g., a movement of the catheter relative to the stenosis or the target position), and to indicate that, or when, the automatic image processing or image evaluation reveals that the catheter has reached the target position, (e.g., the midpoint of the stenosis).

For example, depending upon the type of medical object, the respective patient region in which the medical object is used, the imaging method used and the image quality achieved, when visualizing the image data, precise localization based purely on a visual estimation, for example, on the part of a physician performing the treatment, may be difficult and/or require a time-consuming study of the respective visualization. Automatic image evaluation, which may include automatic edge detection, may achieve higher precision in the localization of the medical object, in particular relative to the target position and/or relative to anatomical features or details, such as a vessel wall. Herein, it is advantageously also possible for a respective scale or scaling of the image data or the visualization to be taken into account automatically so that, for example, it is possible to indicate or display a corresponding distance of the medical object to the target position in absolute metric units. This advantageously enables, for example, misinterpretations based on the failure to take account of a zoom factor to be avoided. Moreover, this advantageously enables the provision of a reliable reference by which the physician may orient him/herself particularly simply, quickly, and precisely when handling the medical device. Overall, this enables the respective medical procedure to be performed with improved safety, reliability, and precision because automatic image processing offers additional objective safeguarding of an interpretation made by the respective physician or medical staff.

While with conventional methods, the image data is frequently only visualized live during the respective procedure on a monitor or screen, the present disclosure provides storage of the detected positions and the corresponding detection times of the medical object in the database thus additionally facilitating subsequent comprehension and analysis of the respective procedure or the respective workflow. For this, it may be advantageous, together with the positions and detection times, also to store respective individual images or video sequences from the image data in the database hence facilitating better illustration of the further stored data and the respective procedure.

The automatic determination and storage of the corresponding data in the database enables the determination or calculation therefrom of further derived data or variables that are not available with conventional methods. This may be an instantaneous or average speed of the medical object and/or a precise time interval between two events. Thus, for example, a period of time between the entry of the medical object and reaching the target position may be automatically determined and displayed when required. Such a period of time, for example, from the insertion of the catheter in the patient until inflation at the target position, may be used as a comparison or quality metric or feature. This, for example, enables the efficiency of the respective procedure and/or of the respective medical staff involved to be determined in a particularly simple and objective manner or used as a comparative variable. This advantageously enables comparability and transparency with respect to available medical applications or suppliers. It is also possible to use such objective metrics for marketing purposes, for example.

However, particularly advantageously, automatic acquisition and storage of the data or variables facilitates not only, for example, statistical evaluation, but also visualization of the respective procedure or the respective workflow, for example, on a dashboard or in a dashboard application. This may take place in real time during the procedure and subsequently. Overall, the automatically acquired, determined, and stored data may advantageously be used, for example, for documentation and/or teaching purposes, wherein, visualization enables the data to be provided or prepared in a form that is particularly easily and clearly understandable to lay people.

Particularly advantageously, a change of state of the medical object, in particular, in conjunction with the respective position and the respective detection time at which or when the change of state takes place may be automatically detected and stored in the database. Such a change in state may be inflation (e.g., ballooning) of the catheter, unfolding of a stent or the like. This may advantageously facilitate more detailed understanding or analysis of the respective procedure.

In an advantageous embodiment, the medical object and the position thereof are detected and tracked by recognizing at least one marker arranged on the medical object. In other words, the position of the medical object may be tracked by the marker, for example, a mark or a locator, on the medical object itself and detected by the image evaluation or image processing of the image data. Herein, a type of marker may be dependent upon the imaging method used in order to provide in each case that the marker is acquired or depicted, e.g., displayed by the respective imaging method. Such a marker may advantageously facilitate particularly precise and reliable detection and localization of the medical object or the position thereof. A corresponding embodiment or arrangement of the marker also enables an alignment or spatial location of the medical object to be reliably and precisely determined. Because the marker may be arranged on a known position of the medical object, the possibility of particularly simple, reliable and precise detection of the marker also enables, for example, respective edges or outer boundaries of the medical object particularly to be localized particularly precisely and reliably. Therefore, the use of the marker enables the method to be carried out more reliably overall and with improved precision or accuracy.

Additionally, or alternatively, it is possible to acquire and process or evaluate manual indications or inputs for tracking the position of the medical object. Thus, for example, the respective member of the medical staff may indicate or input manually that the medical object has reached a certain position or location or a certain state. This may support or safeguard the automatic image evaluation for tracking the position of the medical object in that reliable reference points are created. This facilitates plausibility checking of the automatic detection, position determination, and tracking of the medical object.

In an advantageous embodiment, the medical object is detected prior to the acquisition of the image data, in particular, by reading a QR code and/or RFID-transponder arranged on the medical object. A respective corresponding detection location and detection time are then stored in the database. In other words, the medical object may thus be automatically acquired or tracked prior to contact with the patient. This may advantageously make the entire procedure including a preparation phase completely understandable and analyzable. In particular, it may be provided that, unless it is intentionally left in the patient, the medical object is acquired or detected again in the same manner after removal from the patient. Thus, it is advantageously possible to automatically document in a unique, reliable, and objective manner the medical objects which are located inside the patient or outside the patient and at which times. This enables corresponding errors to be recognized particularly reliably, in particular, also automatically. Thus, for example, it possible to carry out automatic monitoring or automatic comparison with a predetermined procedure (e.g., workflow) in which it is noted for each medical object used whether or not it is intended to remain in the patient.

In particular, for smaller medical objects on which no QR code and/or RFID transponder may be arranged, it is possible to provide automatic image acquisition, for example, by a 3D camera. Herein, camera data generated and provided by the 3D camera may be processed or evaluated similarly to the image data in order to detect and/or track the respective medical object.

In a further advantageous embodiment, the respective present detected position of the medical object, (e.g., the last position determined thereof), is compared with the target position. A respective present distance of the medical object to the target position is then visualized by a traffic light display, wherein, when at least one predetermined distance threshold value is exceeded or fallen below, the traffic light display is automatically switched to another state. In other words, it is, therefore, for example, possible to specify at least two or at least three value intervals for the distance or an amount of the distance. Depending upon the value interval into which respective present distance or the value thereof falls, the traffic light display is switched to a corresponding state or display state assigned to the respective value interval. The different states of the traffic light display may differ at least in that they have different colors.

Similarly, to a conventional light signaling system used for traffic (e.g., traffic light), the traffic light display provided in the present case may have a state with red illumination, a state with yellow illumination, and a state with green illumination. If, for example, the medical object is recognized as a catheter that is moving in the direction of a stenosis, the traffic light display may signal or visualize, (e.g., by red illumination), that the catheter is still located more than 5 mm away from the stenosis or the corresponding target position, for example, midpoint or endpoint of the stenosis. If, as it draws nearer to the stenosis, the catheter arrives at less than, for example, 5 mm from the stenosis, the traffic light display may signal this by switching to yellow illumination. In this example, therefore, a first distance threshold value is specified as 5 mm. The second distance threshold value may be specified as a distance of 2 mm. If the catheter then arrives at less than 2 mm from the stenosis or the corresponding target position, the traffic light display may visualize this by switching to green illumination. Herein, the distance threshold value or values may be adapted or specified differently according to the requirements, application, or situation.

Such an interval-based or distance-threshold-based traffic light display may advantageously enable a respective situation to be recognized particularly quickly and clearly. In order to perceive or recognize the respective color of the traffic light display, it is not necessary, or only necessary to a minimum degree, for the respective member of medical staff for example to divert his/her visual attention onto the traffic light because colors may be reliably perceived and identified in a peripheral visual range without focusing. Furthermore, there is no need for time-consuming and concentration-demanding interpretation of the visualized image data, (e.g., of X-ray images), by the respective member of medical staff or other people, and therefore, they are able to understand the respective procedure particularly easily, for example, for teaching purposes or as lay people.

Particularly advantageously, it is also possible to provide more complex color coding and/or for example, a specific arrangement or sequence of the differently colored luminous signals or signal sources, for example, lamps or light-emitting diodes. This advantageously enables, for example, visualization of the side of the target position on which the medical object is located and/or whether it is moving away from the target position or moving toward the target position. Thus, it is, for example, possible to visualize the fact that, following a phase of approaching the target position, the medical object has now moved beyond the target position. Obviously, the traffic light display may display or include more or less than, for example, three different colors or states. Thus, it is for example, possible to pass through a continuous color band, (e.g., a coherent section of a color space), in synchronism with the detected movement of the medical object, in particular, in relation to the target position. Therefore, while restriction of the traffic light display to a low number of different colors, for example, three, may advantageously enable particularly quick recognition, a larger number of colors or states of the traffic light display may facilitate more precise indication or applicability of the respective distance.

Therefore, the automatic determination of the respective distance and the particularly easily recognizable display thereof by the traffic light display may also be particularly advantageous because automatic determination of the distance, in particular, in the case of relatively poor image quality of the image data and/or visualization, may be more precise than manual or purely visual determination or estimation of the distance by the respective member of medical staff.

Therefore, the traffic light display enables the respective procedure to be carried more quickly and/or with improved accuracy and/or reliability. Furthermore, in particular, with relatively poor image quality, the automatic determination of the distance may still function reliably and precisely so that, for example, the amount of contrast medium administered to the patient may be reduced compared to conventional methods, with which, for example, the respective physician performing the treatment is obliged to rely solely on visual estimation and correct interpretation of the visualized image or X-ray data. Hence, the use of traffic light display may reduce the stress on the patient.

In an advantageous embodiment, the medical object, in particular the type, model and/or material composition thereof, is identified. At least one parameter of a visualization algorithm by which the image data is visualized, (e.g., displayed on a screen), then automatically adapted as a function of the identification of the medical object in order to improve the image quality of the visualization. In other words, therefore, different image optimization may be automatically selected and carried out as a function of the depicted medical object or the properties thereof. For this, it is possible to specify a plurality of settings or values (e.g., presets) for the one or more parameters. However, algorithm-based dynamic adaptation of the respective present or previous value is also possible, for example, until a predetermined criterion has been met or reached. Such criteria may relate to a specific sharpness, a specific signal-to-noise ratio, a specific contrast value or the like. The at least one adapted parameter or the automatic optimization may, if the image data is raw data, be used in a reconstruction of images from this raw data. Additionally, or alternatively, the at least one adapted parameter or the automatic image optimization may be used in postprocessing of, for example, already reconstructed images. Such content-related or content-based optimization or adaptation of the visualization or the image quality may advantageously achieve improved recognition of at least the medical object.

It is also, for example, possible to provide a database or an assignment table, which in each case assigns one or more predetermined, optimum or to-be-used parameters or parameters values to different medical objects and/or material compositions. Herein, following compilation and provision, such a database or table may facilitate a particularly easy and quick improvement in image quality with little computational effort by corresponding adaptation of the visualization or the visualization algorithm.

Herein, it may be particularly advantageous to adapt the at least one parameter differently for different subregions of the image data or different subregions of a respective image generated from the image data. In other words, therefore, different parameter values of the visualization algorithm may be used for different subregions of the respective image depending on whether or not the medical object is visible or depicted in the respective subregion. Different subregions of the respective image may also, for example, be optimized or visualized differently if different medical objects and/or for example, different types of tissue are depicted differently in these different subregions. For example, it is overall possible to improve the image or visualization quality by a content-based evaluation of the image data.

It is, for example, possible to use an automatic object recognition algorithm to identify the medical object from its type, model, and/or material composition. Also possible is, for example, automatic interrogation of a data memory, for example, an electronic patient record or an electronically stored plan of the procedure, from a corresponding data-processing device. This enables the medical objects used to be determined directly or, for example, indirectly via the type of procedure performed. However, optionally, this may restrict the number of possible eligible medical objects thus improving accuracy or reliability of the recognition. Additionally, or alternatively, it is also possible, for example, to acquire a corresponding user input which may indicate or identify the medical object used. It is further additionally or alternatively possible for a specification database to be automatically interrogated in order to—possibly after the identification of the type or model of the medical object—determine further specifications for the medical object, such as, for example, the material composition thereof. It is also possible, for example, to use a spectrometer or to evaluate the available image data by spectrometry in order, for example, to determine the material composition. It is then possible to draw conclusions regarding the type or model of the medical object from the material composition.

To improve the image quality as a function of the identification of the medical object, it is, for example, possible to adapt the filtering, brightness, and/or contrast ratio. It is immediately evident that, for example, metallic medical objects and medical objects made of a plastic material or of glass may be represented very differently in the image data. Taking this circumstance into account may enable the image quality and the ease of recognition to be significantly improved compared to conventional methods, which may use uniform, homogenized image visualization, or image optimization.

In a further advantageous embodiment, the medical object, in particular, the type, model, and/or material composition thereof, is identified and then the radiation power and/or contrast medium feed or dosage used for the medical imaging method automatically controlled as a function of the identification. For example, if the identification reveals that the medical object is made of a metallic material, it is, for example, possible to reduce the radiation power used because metallic objects are or may be sufficiently easy to recognize and/or detect even with reduced radiation power. On the other hand, in order, for example, to make a plastic hose sufficiently easy to recognize, it is, for example, possible for the radiation power to be automatically increased. Thus, it is advantageously possible, according to requirements, to provide maximum or adequate image quality while simultaneously minimizing at least the average stress on the patient, (e.g., reducing or restricting the stress to the necessary level in each case). Herein, the medical object may be identified as already described elsewhere in this document.

In a further advantageous embodiment, when a predetermined object is identified as the medical object and/or when the medical object reaches a predetermined trigger position, a signal indicating or displaying this is automatically generated and emitted in order to initiate or trigger a subsequent method act of a medical method. For example, the detection of a specific medical object indicates that the medical object is located at the detection location, e.g., an acquisition region of a device used for the medical imaging method, such as to generate the image data. In particular, in the case of relatively long and/or multi-act procedures, it is then, for example, possible for a specific specialist to be notified automatically of subsequent acts of the procedure so that he/she may prepare for the assignment with optimum timing or go to an appropriate location for the assignment. In another example, when the medical object has reached the trigger position—which may, but does not have to, correspond to the target position—a control signal may be automatically sent to the imaging device thus automatically triggering, for example, recording with particularly high radiation power and/or resolution of documentation depicting the medical object at the position reached. Such a procedure advantageously enables the course of the respective procedure to be partially automated and hence performed more quickly and/or with a higher degree of reliability or efficiency and/or with reduced personnel costs.

In a further advantageous embodiment, the medical object is moved to the target position by a robot, wherein the robot is controlled as a function of the detected and tracked position of the medical object. In other words, therefore, the automatic evaluation of the image data may result in the creation of a control loop for the automatic positioning of the object at the target position by the robot. Such automation enables, for example, the medical object to be positioned particularly quickly and/or precisely, in particular without jitter, at the target position. Advantageously, the medical object may also be held precisely at the target position by the robot without jitter for as long as desired. This may advantageously improve precision when positioning the medical object and, for example, reduce the risk of injury to the patient. The robot may be an industrial robot or a medical robot with a multi-axis robot arm or manipulator, wherein the robot may have at least six degrees of freedom may in order to facilitate flexible positioning of the medical object. For example, the robot may move a catheter through a vessel of the patient.

In an advantageous embodiment, the image data depicts at least one subregion of a patient and acquires an ECG signal of this patient. The robot is then controlled as a function of the ECG signal in order to compensate a heart movement or respiratory movement derived from the ECG signal. In other words, therefore, a movement or a movement pattern of the patient is automatically determined from the ECG signal and the robot is controlled synchronously to this movement or this movement pattern. This, for example, enables the medical object, despite the heart movement, in particular, if it is located on the heart to remain, or be held or guided in a fixed position, (e.g., relatively still), or in a predetermined spatial relationship relative to the heart or another anatomical feature, (e.g., a vessel wall). This may be achieved or performed by the robot particularly precisely and with high repeat accuracy. Compensating the heart movement or the respective local movement caused by the heart movement advantageously enables unwanted contact between the patient and the medical object to be avoided and thus the risk of injury to the patient to be minimized. At the same time, the stable spatial relationship maintained between the medical object and a part of the patient, for example, the heart, enables a respective medical intervention or manipulation of the patient to be performed particularly precisely and reliably. Herein, it may advantageously be provided that, although the robot moves the medical object such that the heart movement is compensated, it is still possible for the medical object to be moved, for example, by the respective physician performing the treatment.

A tracking system is used or configured for automatic tracking of a medical object. For this, the tracking system includes a first acquisition apparatus, a second acquisition apparatus, an image-processing device, a display apparatus, and a storage apparatus. The first acquisition apparatus is used or configured for the continuous acquisition of image data obtained by a medical imaging method. The second acquisition apparatus is used or configured for the acquisition of a predetermined target position for the medical object. The image-processing device is used or configured for detecting the medical object by processing the image data by an image processing algorithm and for time-resolved tracking of a position of the medical object. The display apparatus is used or configured for indicating that, or when, the detected medical object has reached the target position. The storage apparatus is used or configured to store a plurality of the detected positions of the medical object and associated detection times in a database.

The first and the second acquisition apparatus may be separate apparatuses or combined in one single apparatus.

In particular, the tracking system may be embodied and configured to carry out at least one embodiment of the method. For this, the tracking system may include a storage medium or a data carrier with program code that represents or codes the method acts of the method. The tracking system may furthermore include at least one microchip or microprocessor apparatus configured to execute this program code. The tracking system may also include one or more interfaces and/or at least one user interface via which data and/or inputs may be received or acquired. It is also possible for at least one output interface to be provided in order, for example, to output data or a visualization to an external system or an external database.

The properties and developments of the method disclosed above and in the following and the corresponding advantages may each be transferred analogously to the tracking system and/or to components and apparatuses that are or may be used for the performance of the method and vice versa. Therefore, the disclosure also includes developments of the method and the tracking system including embodiments that are not described explicitly in the respective combination here.

BRIEF DESCRIPTION OF THE DRAWINGS

Further features, details and advantages of the present disclosure may be derived from the following description of the exemplary embodiments and with reference to the drawings, in which.

DETAILED DESCRIPTION

Figure 1:
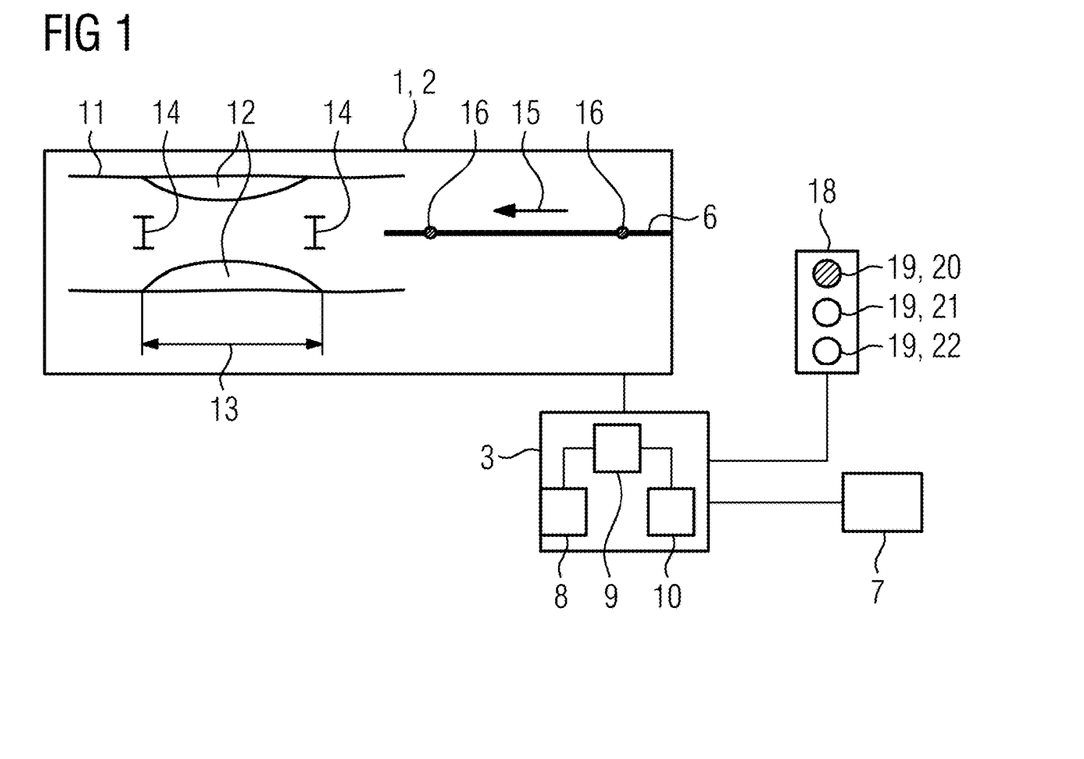
FIG. 1 depicts an example of a schematic and partial illustration of medical image data and a tracking system for tracking a medical object at a first time.

FIG. 1 depicts a schematic and partial illustration of medical image data 1 at a first time 2 and a tracking system 3 for tracking a medical object.

Figure 2:
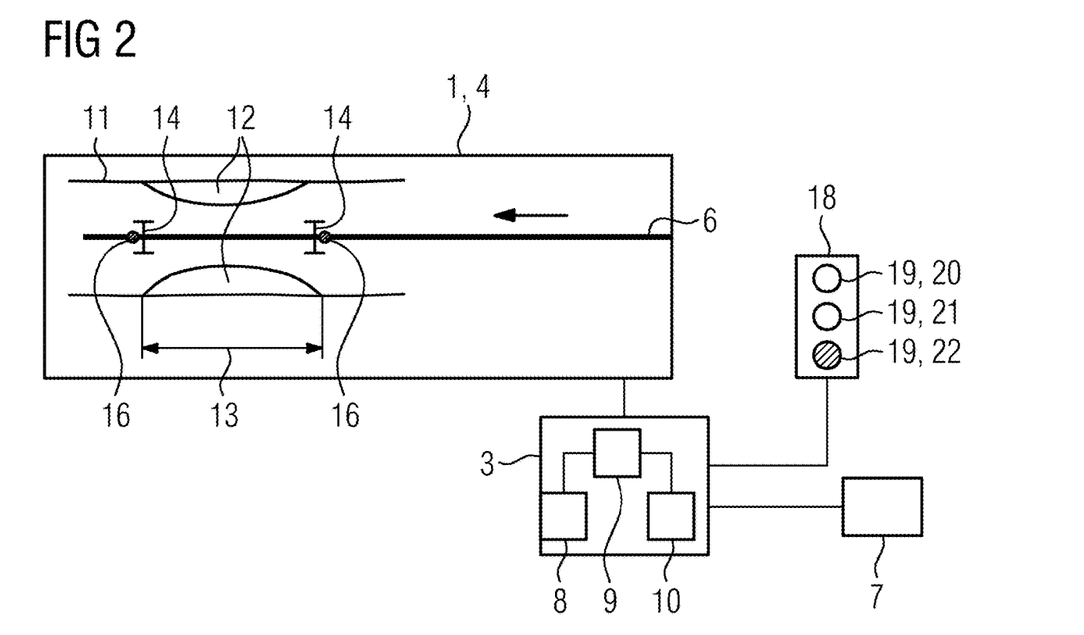
FIG. 2 depicts the schematic illustration in FIG. 1 at a later second time.

FIG. 2 depicts the schematic illustration in FIG. 1 at a later, second time 4.

Figure 3:
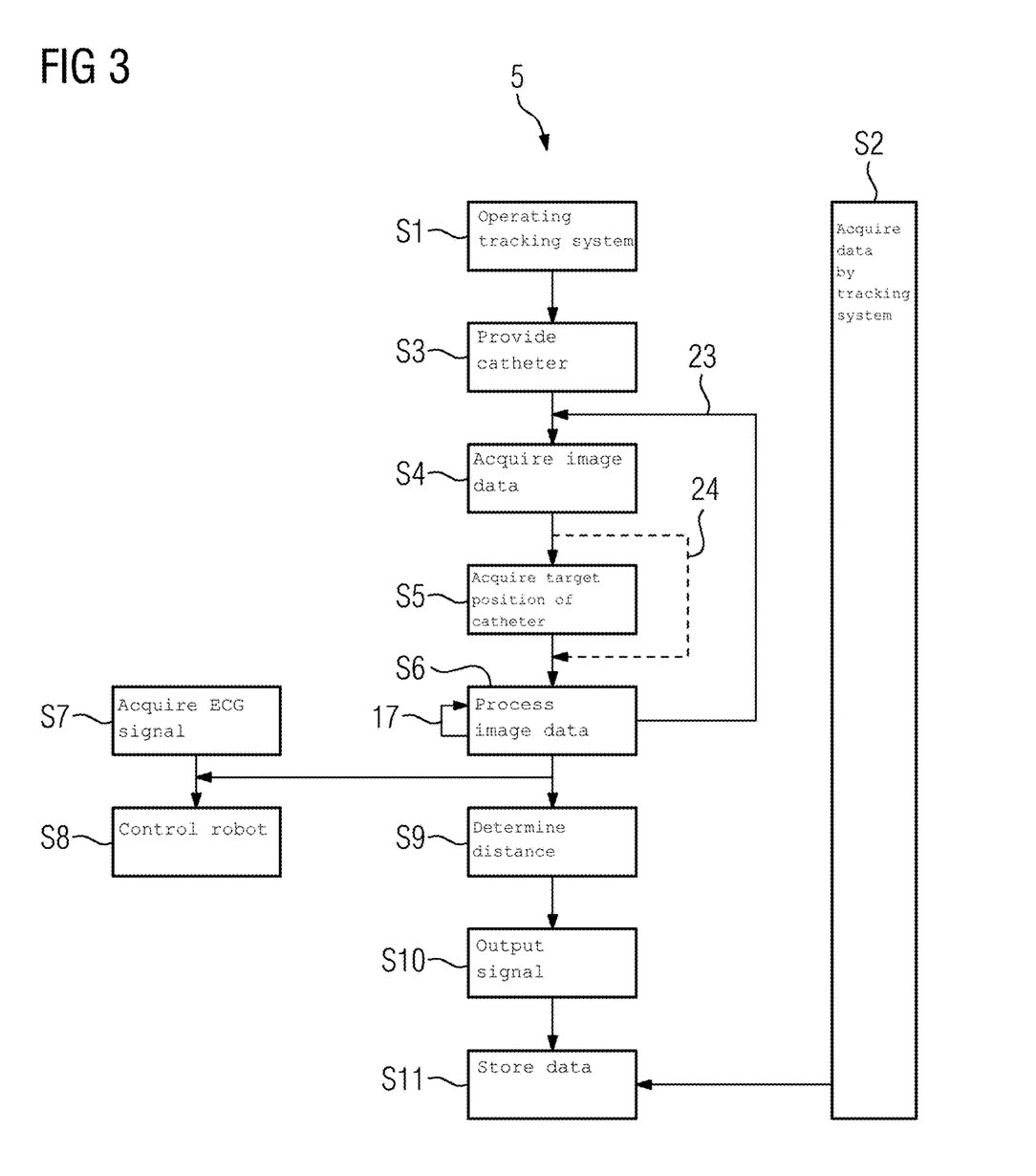
FIG. 3 depicts a schematic exemplary flow diagram of a method for tracking a medical object.

FIG. 3 depicts a schematic exemplary flow diagram 5 of a method for tracking the medical object by the tracking system 3. The following explains the method act of this method with reference to FIG. 1, FIG. 2 and FIG. 3.

The method starts in a method act S1. Here, for example, the tracking system 3 may be put into operation, data required or useful for the further method acts may be prepared or a corresponding database for the tracking system 3 may be made accessible and similar preparatory measures may be performed.

In a method act S2 carried out in parallel to the further method acts, data acquired by the tracking system 3 and optionally generated and optionally provided to the tracking system 3 is visualized. Thus, for example, a respective location and/or status of a respective patient depicted by the medical image data 1 and/or the medical object may be displayed. It is also, for example, possible for respective acts of a procedure relating to the patient, an occupancy status of respective premises used for this purpose, a timeline with events that occur during the procedure and/or similar items to be visualized, (e.g., displayed on a screen or a medical dashboard). This visualization may be color-coded and/or graphically formatted in some other way in order to make all the data relevant for the procedure available in a bundled and understandable form.

In the present example, the medical object may be a catheter 6. The catheter 6 may have a QR code or a RFID transponder or tag, by which the catheter 6 is identified as such. Additionally, or alternatively, for example, an identification number, a model number and/or further data, (for example, relating to a specification of the catheter 6), may be stored or coded in the QR code or in the RFID tag.

In a method act S3, the catheter 6 may be brought or taken to an operating theater in which the patient is subjected to an intervention or treatment as part of the procedure. Herein, the QR code or the RFID tag may be automatically read by the tracking system 3. The tracking system 3 may then, for example, automatically access a data source 7 in order, for example, to use the identification number of the catheter 6 to retrieve further data or specifications relating to the catheter 6. Thus, it is possible for the location of the catheter 6 in the operating theater and optionally further properties of the catheter 6 to be known to the tracking system 3 and accordingly also visualized as early as this stage, (e.g., before the start of the actual intervention on the patient). Hence, it is immediately evident to every person with access to the visualization or the corresponding data on which the visualization is based which medical object is located where and at what time. This may not only make logistics simpler or easier to verify, it is also possible to provide before the start of the actual intervention on the patient that all medical equipment and material required for the procedure is actually available in the operating theater.

Here, it is also possible, for example, for the operating theater to be automatically marked as occupied or displayed in the visualization, for example, when the patient arrives in the operating theater. This may be acquired by the tracking system 3 by automatic scanning, (e.g., reading a QR code on a patient bench).

For the acquisition of this and further data, the tracking system may include an acquisition apparatus 8. The acquired data may be processed by a data-processing device 9 of the tracking system 3. The tracking system 3 may also include a storage apparatus 10 for storing the data and/or corresponding processing results, e.g., the data output by the data-processing device 9. Depending upon the functions or functional scope, the tracking system may also include further apparatuses or components.

The catheter 6 is only used as an example of the medical object; and further or other medical objects, devices, materials, and the like may also be acquired in a corresponding manner.

In a method act S4, the image data 1 may be acquired. For this, the patient may be depicted by an X-ray device or an angiography system. For example, the image data 1 is acquired by a medical imaging method. In addition to a conventional visualization of the image data 1 on a screen or a display, they may be provided to the tracking system 3 or processed thereby.

In the present case, the image data 1 may depict a vessel 11 of the patient with a stenosis 12 of a defined length 13. In a method act S5, the tracking system 3 may acquire a target position for the catheter 6. For this, it is, for example, possible for the physician treating the patient to specify target marks 14 indicating the ideal position, (e.g., the target position), at a start and an end of the stenosis 12. It may also be possible to use automatic image processing of the image data 1 to determine the length 13 of the stenosis 12 and/or for example, a midpoint of the stenosis 12 automatically.

During the intervention, the physician now introduces the catheter 6 into the patient, in particular, into the vessel 11. Accordingly, the catheter 6 is acquired together with the vessel 11 by the imaging method and is therefore also depicted in the image data 1. Here, a movement of the catheter 6 in the direction of the stenosis 12 is indicated by a corresponding arrow 15.

In a method act S6, the image data 1 is processed by the tracking system 3, for example, by an object recognition algorithm. Herein, the tracking system is able to detect the catheter 6 automatically and determine its position, in particular, relative to the target position or the stenosis 12. For this, the catheter 6 may have radio-opaque markers 16 which may simplify the detection of the catheter 6 and/or the determination of its position. Herein, the tracking system 3 is able not only to automatically recognize that a medical object is depicted in the image data 1, but also to identify that this is the catheter 6. For this, it is, for example, able to process or take account of data that has been provided in advance and/or retrieved from the data source 7 and/or from the storage apparatus 10. Therefore, the tracking system 3 may recognize or determine what is visualized in the image data 1. Because the tracking system 3 is also able continuously to analyze the continuously updated image data 1, the tracking system is able to track the respective present position of the catheter 6 continuously as indicated in the flow diagram 5 by a first loop 17.

In particular, in method act S9, the tracking system 3 may determine and continuously update a distance from the catheter 6 in its respective present position to the target position. This distance may be determined or defined in different ways according to requirements. Thus, the distance determined may be the distance between the tip of the catheter 6 and a midpoint of the stenosis 12. Herein, the midpoint of the stenosis 12 may be calculated by adding half the length 13 to a position of one of the target marks 14 in the direction of the other target mark 14. It is also possible, for example, for the distance determined to be the distance that still has to be traversed by catheter 6 in the direction of the stenosis 12 or the target position in order to bring the markers 16 into a position coincident with the target marks 14 or a position symmetrical to the target marks 14.

The tracking system 3 is able to actuate a display apparatus, in the present case embodied as a traffic light display 18, as a function of the respective currently determined distance of the catheter 6 from the target position. In the present case, this traffic light display 18 includes, by way of example, three display elements 19. Of these, for example, a first display element 20 may be switched to a red illuminated state, a second display element 21 to a yellow illuminated state, and a third display element 22 to a green illuminated state. In the present case, at first time 2 shown in FIG. 1, the distance is more than for example, 5 mm or for example, more than 10 mm. Therefore, at the first time 2, the traffic light display 18 is switched to a state in which the traffic light display 18 indicates this distance value by a red illumination of the first display element 20.

For example, a radiation power used to generate the image data 1 and/or contrast medium feed may be automatically adapted as a function of an identification of the catheter 6 determined by the tracking system 3 and/or as a function of the determined distance of the catheter 6 to the target position. It is also possible, for example, for a visualization algorithm used to reconstruct and/or display the image data 1 to be adapted as a function of the determined identification of the catheter 6 in order to achieve optimum image quality. These adaptations are indicated by a second loop 23 in the flow diagram 5.

Following the adaptation of the radiation power, the contrast medium feed and/or the visualization algorithm, it is possible to generate or acquire and/or visualize further image data. Then, it may not be necessary to acquire or determine the predetermined target position again. Therefore, it may be possible for the method act S5 to be performed once only during the procedure or during the method or once only for each medical object as indicated by a path 24 in the flow diagram 5.

In parallel to one, some or all of the previous and/or following method acts, an ECG signal of the patient may be acquired in a method act S7, for example.

In a method act S8, a robot may be controlled or actuated as a function of this ECG signal or heart or respiratory movement of the patient derived therefrom and/or as a function of the determined identification of the catheter 6 and/or as a function of the image data 1 or data processing results derived therefrom, such as the position of the catheter 6 or relative position or location with respect to the target position. In the present example, therefore, this robot may be coupled to the tracking system 3. The robot may be used to hold the catheter 6 and in particular move it into or toward the target position.

If, during this movement, the distance of the catheter 6 to the target position falls below the predetermined distance threshold value of, for example, 5 mm or 10 mm, this is automatically indicated by yellow illumination of the second display element 21. Then, the red illumination of the first display element 20 may be canceled or switched off.

In the present case, the catheter 6 has reached the target position at the second time 4 shown schematically in FIG. 2. Accordingly, the catheter 6 has been moved so far in the direction of the target position, which is indicated by the target marks 14 or predetermined, that the positions of the markers 16 of the catheter 6 are, as far as possible, brought into a position coincident with the target marks 14 or into a symmetrical position or arrangement to the greatest degree as possible. Arrival at the target position is automatically indicated by the tracking system 3 by actuating the traffic light display 18 or by switching to green illumination of the third display element 22. Because, therefore, the relative location of the catheter 6 to the stenosis 12 or to the target position by the traffic light display 18 is displayed in a manner that is particularly easy to recognize, the traffic light display 18 or the tracking system 3 may, therefore, clearly serve or be understood as a navigation or parking aid for the respective physician performing the treatment, in particular when the catheter 6 is moved by the actual physician or by operating the robot.

The target position or another predetermined position may also be defined as a trigger position, which, when reached by the catheter 6, causes the tracking system 3 to automatically generate a corresponding signal and output this signal in a method act S10. This signal may then initiate or trigger a further act of the procedure.

Following completion of the intervention on the patient, the tracking of the medical instruments used, (e.g., the catheter 6), it may be provided automatically and objectively that no medical objects have been left in the patient unintentionally. For this, it is, for example, possible to read a respective QR code or RFID tag again outside the patient.

The data acquired, processed, generated and visualized by the tracking system 3 during the method or during the procedure may be stored in a method act S11, for example, in the storage apparatus 10. Obviously, the corresponding data may also be stored directly during the preceding method acts during or after their respective availability. This stored data may then be used as the basis for visualizing the procedure or a corresponding workflow and/or, for example, also facilitate analysis at a later time.

Overall, therefore, compared to previous methods, it is particularly advantageous, not only to display the image data 1 during the procedure, but to perform automatic evaluation, processing and storage and, to this end, to forward the corresponding data to the tracking system 3.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for tracking a medical object, the method comprising:
   continuously acquiring image data obtained by a medical imaging method comprising recording a series of X-ray images by an X-ray device;
   acquiring a predetermined target position point for the medical object comprising an automatic analysis by an image processing algorithm to determine a length of a stenosis and calculate a midpoint of the stenosis as the predetermined target position point configured to be reached by the medical object;
   automatically detecting the medical object and performing time-resolved tracking of the respective position of the medical object, by the image processing algorithm, to indicate respective positions of the medical object at respective recording times of the image data;
   indicating that the detected medical object has reached the predetermined target position point;
   automatically adjusting a radiation power or a contrast medium feed of the X-ray device for the medical imaging method in response to a determination of a distance of the detected medical object with respect to the predetermined target position point;
   indicating a respective recording time of the image data when the detected medical object has reached the predetermined target position point; and
   storing a plurality of the detected respective positions of the medical object and the respective recording times of the image data associated with the detected respective positions of the medical object in a database,
   wherein the medical object is a catheter, a stent, or a medical screw, and
   wherein the medical object is further detected prior to the acquiring of the image data and prior to contact of the medical object with a patient.

2. The method of claim 1, wherein the medical object and the respective positions of the medical object are detected and tracked by recognizing at least one marker arranged on the medical object.

3. The method of claim 1, wherein the medical object is detected prior to the acquiring of the image data by reading a Quick Response (QR) code and/or Radio-Frequency Identification (RFID) transponder arranged on the medical object, and a respective corresponding detection location and detection time are stored in the database.

4. A method for tracking a medical object, the method comprising:
   continuously acquiring image data obtained by a medical imaging method comprising recording a series of X-ray images by an X-ray device;
   acquiring a predetermined target position point configured to be reached by the medical object, wherein the predetermined target position point is a reference point of an anatomical feature of a patient;
   automatically detecting the medical object and performing time-resolved tracking of the respective position of the medical object, by an image processing algorithm, to indicate respective positions of the medical object at respective recording times of the image data;
   comparing a presently detected respective position of the medical object with the predetermined target position point;
   displaying, by a traffic light display, a respective present distance of the medical object to the predetermined target position point, wherein the traffic light display comprises a plurality of display elements of different colors, wherein the traffic light display is automatically switched between one display element of the plurality of display elements to another display element of the plurality of display elements when at least one predetermined distance threshold value is fallen below, therein indicating that the present distance of the medical object has moved within threshold distance of the predetermined target position point;

adjusting a contrast medium feed of the X-ray device for the medical imaging method in response to a determination of the present distance of the medical object with respect to the predetermined target position point and the traffic light display switching to the other display element;

indicating that the detected medical object has reached the predetermined target position point; and storing a plurality of the detected respective positions of the medical object and the respective recording times of the image data associated with the detected respective positions of the medical object in a database, wherein the medical object is further detected prior to the acquiring of the image data and prior to contact of the medical object with the patient.

5. The method of claim 1, further comprising:
identifying the medical object; and
automatically adapting at least one parameter of a visualization algorithm, by which the image data is visualized, as a function of the identification in order to improve an image quality of the visualization.

6. The method of claim 5, wherein the identifying of the medical object comprises identifying one or more of a type, a model, or a material composition of the medical object.

7. The method of claim 1, further comprising:
identifying a type, a model, or a material composition of the medical object; and
automatically controlling the radiation power used for the medical imaging method or the contrast medium feed as a function of the identification.

8. The method of claim 1, further comprising:
automatically generating and emitting a signal when the medical object reaches the predetermined target position point, wherein the signal indicates the reaching of the predetermined target position point, and wherein the signal is generated and emitted in order to initiate a subsequent act of the method.

9. The method of claim 1, further comprising:
moving the medical object, by a robot, to the predetermined target position point,
wherein the robot is controlled as a function of the detected and tracked respective position of the medical object.

10. The method of claim 9, further comprising:
depicting the image data having at least one subregion of the patient;
acquiring an electrocardiogram (ECG) signal from the patient; and
controlling the robot as a function of the ECG signal in order to compensate a heart movement of the patient derived from the ECG signal.

11. The method of claim 1, wherein the medical object is the catheter, and
wherein the predetermined target position point is the stenosis.

12. The method of claim 1, wherein the automatically adjusting comprises automatically increasing the radiation power or the contrast medium feed.

* * * * *